(12) United States Patent
Purcell et al.

(10) Patent No.: US 7,913,696 B2
(45) Date of Patent: *Mar. 29, 2011

(54) SELF-FITTING DEVICE FOR LOCATION IN AN EAR CANAL

(75) Inventors: Ricky Wayne Purcell, Alpharetta, GA (US); Kenneth Michael Ross, Chicago, IL (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 152 days.

This patent is subject to a terminal disclaimer.

(21) Appl. No.: 12/217,083

(22) Filed: Jun. 30, 2008

(65) Prior Publication Data

US 2009/0320859 A1    Dec. 31, 2009

(51) Int. Cl.
*A61F 11/00* (2006.01)
*H04R 25/02* (2006.01)
*H04R 25/00* (2006.01)

(52) U.S. Cl. ........ 128/864; 181/130; 181/135; 381/328; 381/329; 381/322

(58) Field of Classification Search .......... 128/864–868; 181/135, 130; 623/10; 381/322, 328–329, 381/72
See application file for complete search history.

(56) References Cited

U.S. PATENT DOCUMENTS

| | | | |
|---|---|---|---|
| 2,246,736 A | 6/1941 | Knudsen | |
| 2,824,558 A | 2/1958 | Michael et al. | |
| 2,850,012 A | 9/1958 | Becker | |
| 2,876,767 A * | 3/1959 | Wasserman | 128/865 |
| 3,123,069 A | 3/1964 | Laisne et al. | |
| 3,736,929 A | 6/1973 | Mills | |
| 4,060,080 A | 11/1977 | Akiyama | |
| 4,133,984 A | 1/1979 | Akiyama | |
| 4,582,053 A | 4/1986 | Wilson | |

(Continued)

FOREIGN PATENT DOCUMENTS

| | | |
|---|---|---|
| EP | 1276443 B1 | 3/2006 |
| EP | 1 653 776 A2 | 5/2006 |
| GB | 1 423 194 A | 1/1976 |

(Continued)

OTHER PUBLICATIONS

Patent Cooperation Treaty Search Report from the International Search Authority, International Application No. PCT/IB2009/052711 dated Feb. 23, 2010.

*Primary Examiner* — Patricia M Bianco
*Assistant Examiner* — Tarla R Patel
(74) *Attorney, Agent, or Firm* — Michael J. Bendel; Nathan P. Hendon; Nancy M. Klembus (57) ABSTRACT

A self-fitting device for location in an ear canal. The device includes a body having a body ear end, an opposite body user end, and a shaft extending from the ear end to the user end. A resilient bladder is joined with the body ear end and a chamber is defined inside the resilient bladder. An elongate plunger is located in the shaft. The resilient bladder is deformable between an at-rest position and an in-ear position. The elongate plunger actuates between the at-rest position and an insertion position to assist the resilient bladder to be deformed into the in-ear position. The plunger actuates in the insertion position without extending a front end portion of the bladder forward of a position of the front end portion when the bladder is in the at-rest position.

22 Claims, 6 Drawing Sheets

U.S. PATENT DOCUMENTS

| | | | | |
|---|---|---|---|---|
| 4,913,165 | A | 4/1990 | Fishgoyt | |
| 5,293,008 | A * | 3/1994 | Danielsen | 181/135 |
| D364,455 | S | 11/1995 | Krause | |
| D366,313 | S | 1/1996 | Krause | |
| D366,696 | S | 1/1996 | Krause | |
| 5,483,027 | A | 1/1996 | Krause | |
| 6,006,857 | A * | 12/1999 | Leight et al. | 181/135 |
| 6,256,396 | B1 * | 7/2001 | Cushman | 181/135 |
| 6,942,696 | B1 | 9/2005 | White et al. | |
| 7,362,875 | B2 * | 4/2008 | Saxton et al. | 381/322 |
| 2008/0144871 | A1 * | 6/2008 | Purcell et al. | 381/329 |
| 2008/0264428 | A1 * | 10/2008 | Purcell et al. | 128/864 |
| 2009/0173353 | A1 | 7/2009 | Purcell et al. | |
| 2009/0320858 | A1 * | 12/2009 | Purcell et al. | 128/864 |

FOREIGN PATENT DOCUMENTS

| | | |
|---|---|---|
| GB | 2 323 295 A | 9/1998 |
| JP | 06-343659 A | 12/1994 |
| JP | 10-094615 A | 4/1998 |
| JP | 2002-000637 A | 1/2002 |
| WO | WO 98/25558 A1 | 6/1998 |
| WO | WO 2004/100608 A2 | 11/2004 |
| WO | WO 2008/075221 A1 | 6/2008 |

* cited by examiner

SELF-FITTING DEVICE FOR LOCATION IN AN EAR CANAL

BACKGROUND OF THE INVENTION

The present invention relates generally to devices for location in an ear canal, and more particularly to such devices being self-fitting and used for sound optimization such as noise reduction and/or acoustic enhancement.

The need for adequate hearing protection in high noise environments has long been recognized among those concerned with health and safety issues, and much effort has gone into providing such protection. However, most experts in this field would acknowledge that this effort has not been completely successful. Protective devices have proliferated yet remain needing better performance. Workers in high noise environments who should use these devices often do not, or use them only under duress from their employers. Individuals that work in high noise environments rarely understand that the effects of high noise exposure are not limited to the moment but are cumulative as well. The lack of worker compliance with safety rules is exacerbated by the fact that currently available hearing protection devices are often uncomfortable, clumsy to use, and/or perform poorly. Fortunately, as hearing protection devices become more comfortable and perform better, worker compliance with their use should also improve.

For example, existing disposable foam ear plugs are uncomfortable for wearers with small ear canals, are difficult to properly insert, must be completely removed if noise reduction is unwanted for a brief period (e.g. conversation), and/or cause discomfort during removal. Common disposable foam ear plugs require the user to compress the volume of the plug and insert it into the ear canal where it then attempts to re-expand. This method can cause discomfort for people with small ear canals in that the more compressed the ear plug, the greater its exerted force toward re-expansion. Further, existing disposable foam ear plugs require the user to roll the foam between their fingers to compress the foam to a sufficient size for proper insertion. If this step is not done, or is insufficiently done, the ear plug is often inserted improperly so as to not provide optimal protection. Also, if the user has dirty hands when compressing the ear plug, dirt and/or germs are then put into the ear canal with the inserted ear plug. Further, existing disposable foam ear plugs must be completely removed if the user needs increased use of their hearing faculties for a brief period such as engaging in conversation with a coworker. This could lead to improper reinsertion if the earplugs are removed or misunderstanding of potentially important information if not removed. And, existing foam ear plugs are often designed for one time use.

Accordingly, while various types of in-ear devices exist in the art, there remains a need for an in-ear device that helps overcome one or more of the aforementioned problems. The applicants have surprisingly invented such a device, as discussed further herein.

SUMMARY OF THE INVENTION

Various definitions used throughout the specification and claims are provided first, followed by a description of various aspects of the invention.

As used herein, "resilient" means that property of a material or composite material that permits it to be deformed in size and/or shape and then recover at least about 80% of its original size and shape no later than two minutes after removal of the force causing the deformation.

As used herein, "non-resilient" means the opposite of resilient.

In one aspect of the present invention, there is provided a self-fitting device for location in an ear canal. The device includes a body having a body ear end, an opposite body user end, and a shaft extending from the ear end to the user end. A resilient bladder is joined with the body ear end and a chamber is defined inside the resilient bladder where the chamber is in communication with the shaft. An elongate plunger is located in the shaft, the elongate plunger having a plunger user end extending out of the shaft and away from the body ear end and an opposite plunger ear end in communication with the chamber. The resilient bladder is deformable between an at-rest position and an in-ear position, such that the resilient bladder has a first cross-sectional area in the at-rest position and a second cross-sectional area in the in-ear position, and where the first cross-sectional area is greater than the second cross-sectional area. The elongate plunger actuates between the at-rest position and an insertion position to assist the resilient bladder to be deformed into the in-ear position, and the plunger actuates in the insertion position without extending a front end portion of the bladder forward of a position of the front end portion when the bladder is in the at-rest position.

In another aspect of the present invention, there is provided a self-fitting device for location in an ear canal. The device includes a body having a body ear end, an opposite body user end, and a shaft extending from the ear end to the user end. A resilient bladder is joined with the body ear end and a chamber is defined inside the resilient bladder where the chamber is in communication with the shaft. An elongate plunger is located in the shaft, the elongate plunger having a plunger user end extending out of the shaft and away from the body ear end and an opposite plunger ear end in communication with the chamber. The resilient bladder is deformable between an at-rest position and an in-ear position, such that the resilient bladder has a first cross-sectional area in the at-rest position and a second cross-sectional area in the in-ear position, and where the first cross-sectional area is greater than the second cross-sectional area. The elongate plunger actuates between the at-rest position and an insertion position to assist the resilient bladder to be deformed into the in-ear position. The plunger actuates to engage the resilient bladder in the insertion position and actuates to separate from the resilient bladder in the in-ear position.

In still another aspect of the present invention, there is provided a self-fitting device for location in an ear canal. The device includes a body having a body ear end, an opposite body user end, and a shaft extending from the ear end to the user end. A resilient bladder is joined with the body ear end and a chamber is defined inside the resilient bladder where the chamber is in communication with the shaft. An elongate plunger is located in the shaft, the elongate plunger having a plunger user end extending out of the shaft and away from the body ear end and an opposite plunger ear end in communication with the chamber. The resilient bladder is deformable between an at-rest position and an in-ear position, such that the resilient bladder has a first cross-sectional area in the at-rest position and a second cross-sectional area in the in-ear position, and where the first cross-sectional area is greater than the second cross-sectional area. The elongate plunger actuates between the at-rest position and an insertion position to assist the resilient bladder to be deformed into the in-ear position. When the plunger is in the insertion position a tip of the plunger ear end engages the bladder and when the plunger is in the in-ear position the tip of the plunger ear end is spaced from the bladder.

Other features of the invention relate to particular configurations of the elongate plunger per se and when in the various at-rest, in-ear and insertions positions.

Still other features of the invention will be in part apparent and in part pointed out hereinafter as well as better understood by practice of the invention. It is to be understood that both the foregoing general description and the following detailed description are exemplary and are intended to provide further explanation of the invention claimed. The accompanying drawings, which are incorporated in and constitute part of this specification, are included to illustrate and provide a further understanding of the self-fitting device for location in an ear canal that is the present invention.

BRIEF DESCRIPTION OF THE DRAWINGS

Corresponding reference characters indicate corresponding parts throughout the drawings.

DETAILED DESCRIPTION

Referring now to the drawings and in particular FIGS. 1-9 for example, there is depicted a self-fitting device 10 for location in an ear canal 12. Particularly in FIG. 4-6, there is seen outer ear 13 joined to the portion of the ear canal 12 through which the device 10 is inserted for use, and where the ear drum (not seen) is located at the other end of the ear canal spaced from the device when inserted into the ear canal. Device 10 includes a body 20, a resilient bladder 30 and an elongate plunger 40. Body 20 includes a body ear end 22 and an opposite body user end 24. A shaft 26 extends from the ear end to the user end. More advantageously, though not required, the shaft can have closed sides and the elongate plunger extends through and between the ear end and the user end.

Resilient bladder 30 can be joined with the body ear end 22 of body 20. For example, these two parts could be formed together of one material, or formed of separate materials that are sequentially formed together, or formed separately and then joined together by any conventional means (e.g., adhesive, chemical or heat or other similarly resulting mechanical bonded relationship). A chamber 32 (seen best in FIGS. 8-9 and 12-14) is defined inside the resilient bladder. Chamber 32 is in communication with shaft 26 when bladder 30 is joined with body 20.

Figure 10:
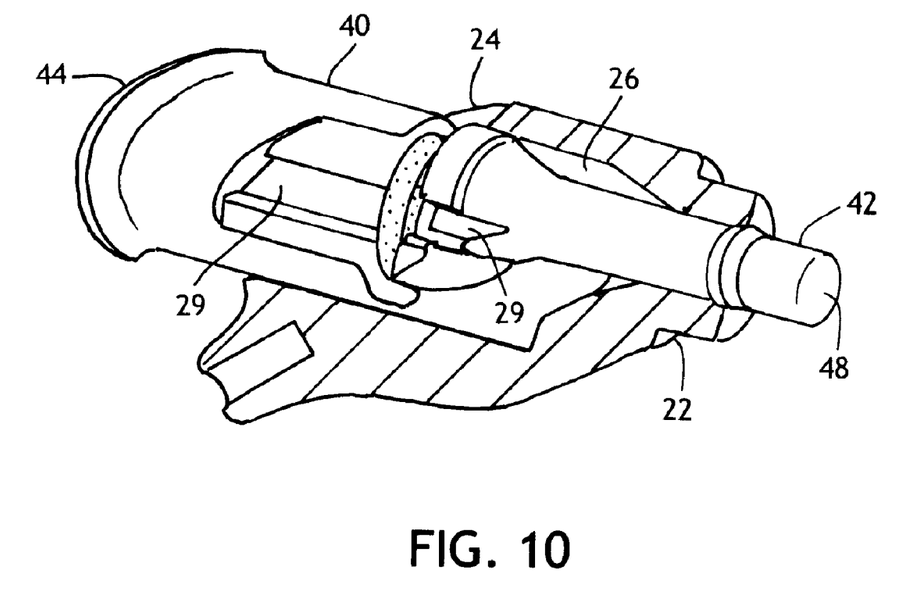
FIG. 10 is a cut away side view of the present invention in the at-rest position.
Figure 11:
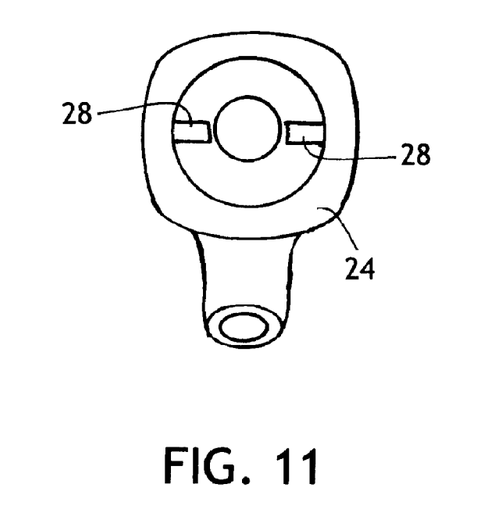
FIG. 11 is an end view of the body portion seen in FIG. 10, looking from the body user end into the shaft.
Figure 12:
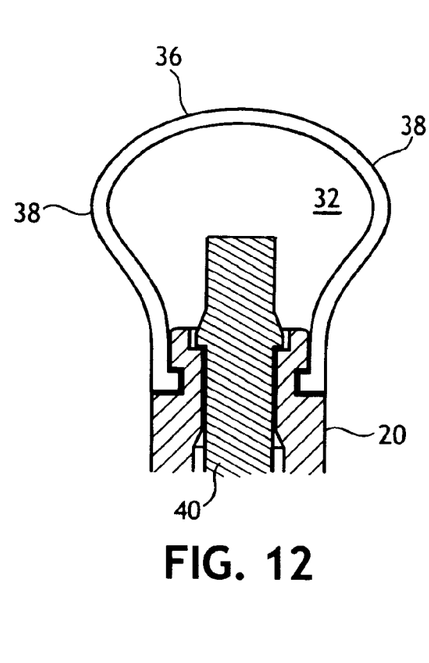
FIG. 12 is a cross-sectional side view of a portion of the device in FIG. 9, shown in an assembled configuration and the device in the at-rest position.

Also referring to FIGS. 10-11, elongate plunger 40 is located in shaft 26. The elongate plunger has a plunger user end 44 which extends out of the shaft, when the plunger is located inside the shaft, and away from the body ear end 22. Plunger 40 also has an opposite plunger ear end 42 able to be in communication with the resilient bladder, when the plunger is located inside the shaft. For example, the communication may be via a pressure type relationship and not direct contact of plunger with bladder, or plunger ear end 42 may engage the resilient bladder.

Elongate plunger 40 actuates between the at-rest position and the insertion position to assist the resilient bladder 30 to be deformed into the in-ear position. More particularly, this can be accomplished in a variety of ways, and some examples are set forth here. The plunger may actuate in the insertion position without extending a front end portion 36 of the bladder forward of a position of the front end portion when the bladder is in the at-rest position. Such is particularly seen in comparing FIG. 1 versus 2 and FIG. 4 versus 5. Explained further, this means that the plunger may act upon, e.g., abut against, the bladder and cause it to maintain the end portion 36 in essentially the same position whether in the at-rest position or the insertion position, or, at least not cause the end portion 36 to be extended outwardly away from the body more in the insertion position than in the at-rest position or vice versa. It is also noted that this aspect of the invention speaks only to action of the plunger upon the bladder, and does not prohibit the bladder front end portion from being extended outwardly away from the body more in the insertion position than in the at-rest position or vice versa, due to causes of the ear or ear canal 12 acting upon the bladder. The invention may also include, advantageously, that the entire plunger ear end is spaced from the bladder at all times except when the plunger is in the insertion position.

Figure 13:
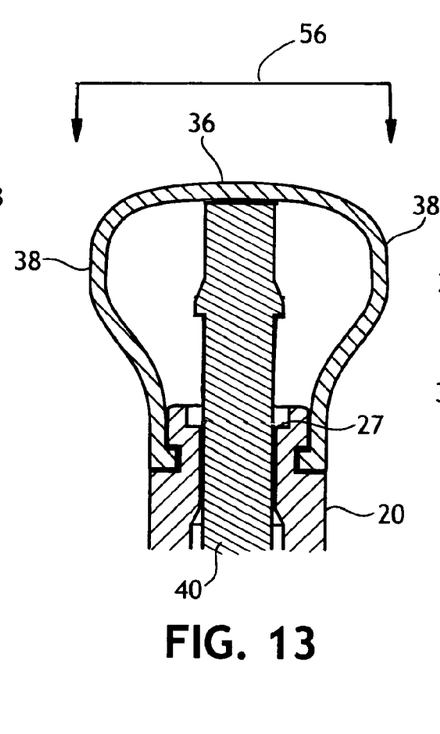
FIG. 13 is a cross-sectional side view of a portion of a device like that in FIG. 9, but with an alternate resilient bladder configuration.
Figure 14:
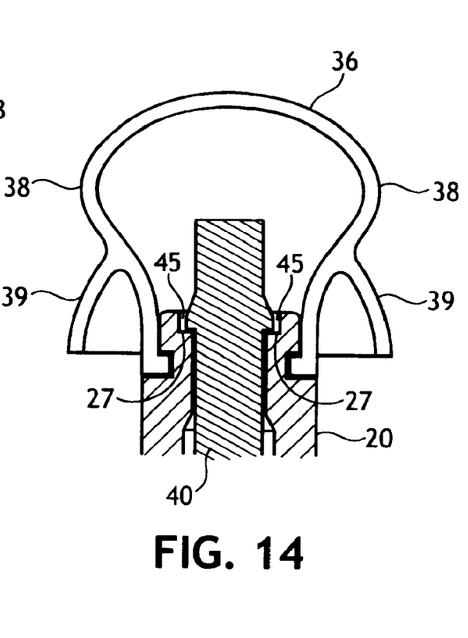
FIG. 14 is a cross-sectional side view of a portion of a device like that in FIG. 9, but with an alternate resilient bladder configuration.

An alternative way the plunger assists the bladder into the in-ear position can be described as when the plunger is in the insertion position a tip 48 of plunger ear end 42 engages the bladder 30 and when the plunger 40 is in the in-ear position the tip of the plunger ear end is spaced from the bladder. Such is particularly seen in comparing FIG. 12 versus 13. Explained further, this means that essentially it is the tip 48 that acts upon, e.g., engages, the bladder when in the insertion position, but more of the plunger could so engage if desired. Then when the plunger is in the in-ear position (and advantageously all positions other than the insertion position), the tip 48 is spaced from the bladder, and advantageously but not required, the entire plunger portion inside the chamber is spaced from the bladder, to help provide more comfort and/or flexibility to the bladder in the in-ear position.

And in yet another alternative way, the plunger assists the bladder into the in-ear position can be described as the plunger actuates to engage the resilient bladder in the insertion position and actuates to separate from the resilient bladder in the in-ear position. Such is particularly seen in comparing FIG. 12 versus 13. Explained further, this means that some portion of the plunger acts upon, e.g. engages, the bladder when in the insertion position. Then when the plunger is in the in-ear position (and advantageously all positions other than the insertion position), the plunger, and advantageously the entire plunger inside the chamber, is spaced from the bladder, to help provide more comfort and/or flexibility to the bladder in the in-ear position.

The resilient bladder 30 is deformable between an at-rest position (e.g., FIGS. 1, 4, 7, 10, 12 and 14) to an in-ear position (FIGS. 3 and 6) to an insertion position (FIGS. 2, 5, and 13) such that the resilient bladder has a first cross-sectional area 50 in the at-rest position and a second cross-sectional area 52 in the in-ear position. Optionally, the resilient bladder may have a third cross-sectional area (not shown) in the insertion position. First cross-sectional area 50 is greater than second cross-sectional area 52. And, if the optional third cross-sectional area is employed, second cross-sectional area 52 may be greater than the third cross-sectional area. The cross-sectional area is determined using the plane orthogonal to the length (longest dimension) of device 10 and parallel to respective area lines 50 and 52, and then measuring the largest area of the portion of the resilient bladder that would engage (at-rest and insertion positions) or does engage (in-ear position) the inside of the ear canal, taking view 56 (FIG. 13). It is noted that the shapes of the bladder seen in FIGS. 1-6 are illustrative of the relative differences between at-rest, insertion, and in-ear positions, but such shapes are not so limited (e.g., the bladder in FIGS. 3 and 6 may be more or less bulbous but would be less bulbous than that in FIGS. 1 and 4).

The body may be formed of a material having a first hardness value and the elongate plunger formed of a material having a second hardness value, and in any case, advantageously both these values are harder than that of the resilient bladder. The first hardness value may be different than the second hardness value, e.g., the first hardness value (of the body) being greater than the second hardness value (of the plunger). For example, the body may be made of a material being about 100 Shore A and the plunger may be made of a material being about 90 Shore A.

The resilient bladder may be made of a homogeneous material or a composite material, and may include one or more layers. Bladder 30 may be made of a polyurethane foam with a "skin" formed on the outside. It may be made from a flexible material that is injection or blow moldable into a bulb that does not permanently deform when stressed by squeezing. Examples could be polyurethane, polyvinylchloride, santoprene, polyethylene, or polypropylene, and these may be in a foam or non-foam form.

Figure 1:
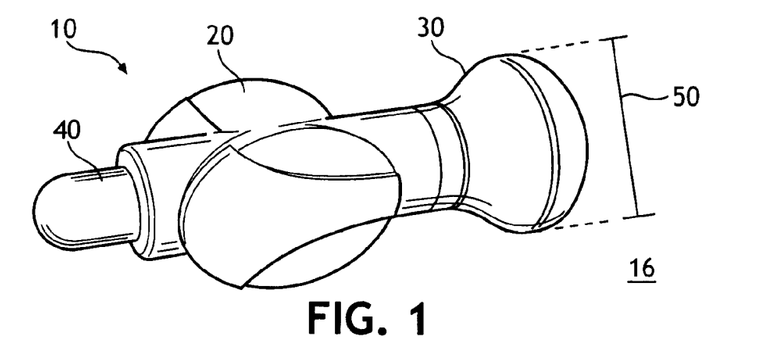
FIG. 1 is a perspective view of the present invention in the at-rest position.
Figure 2:
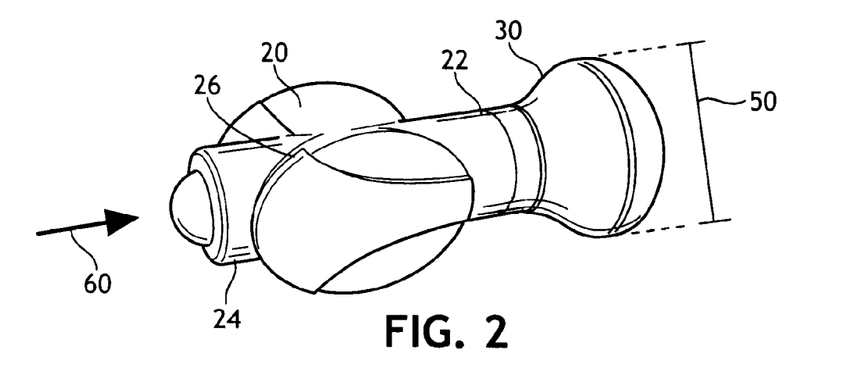
FIG. 2 is a perspective view of the device in FIG. 1, but now in the insertion position.
Figure 3:
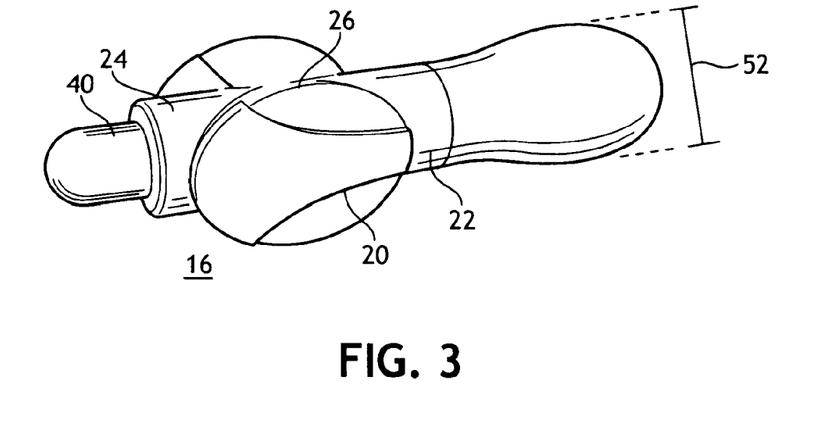
FIG. 3 is a perspective view of the device in FIG. 1, but now in the in-ear position.
Figure 4:
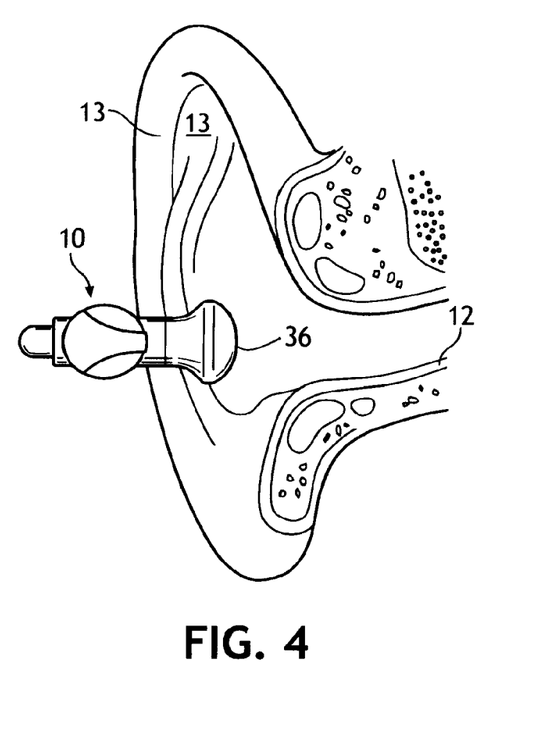
FIG. 4 is a perspective view of the device in FIG. 1, as it is approaching and being made ready for insertion in an ear canal.
Figure 5:
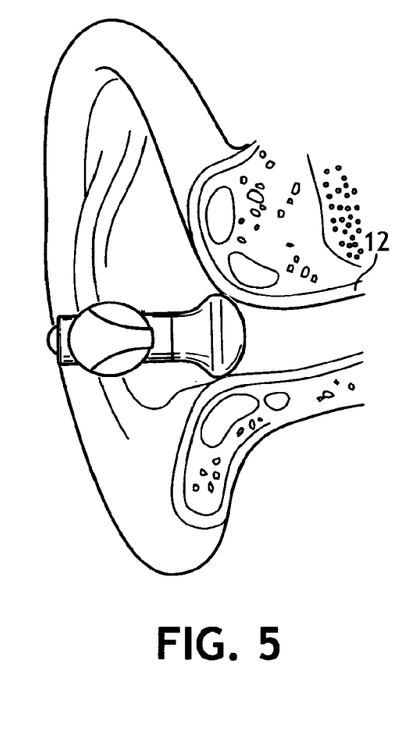
FIG. 5 is a perspective view of the device in FIG. 4, as it is being inserted in the ear canal, with the device in the insertion position.
Figure 6:
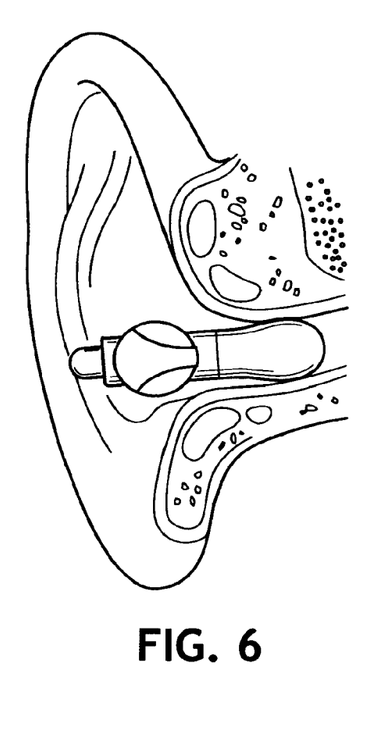
FIG. 6 is a perspective view of the device in FIG. 5, as it is now fully inserted in the ear canal and with the device in the in-ear position.
Figure 7:
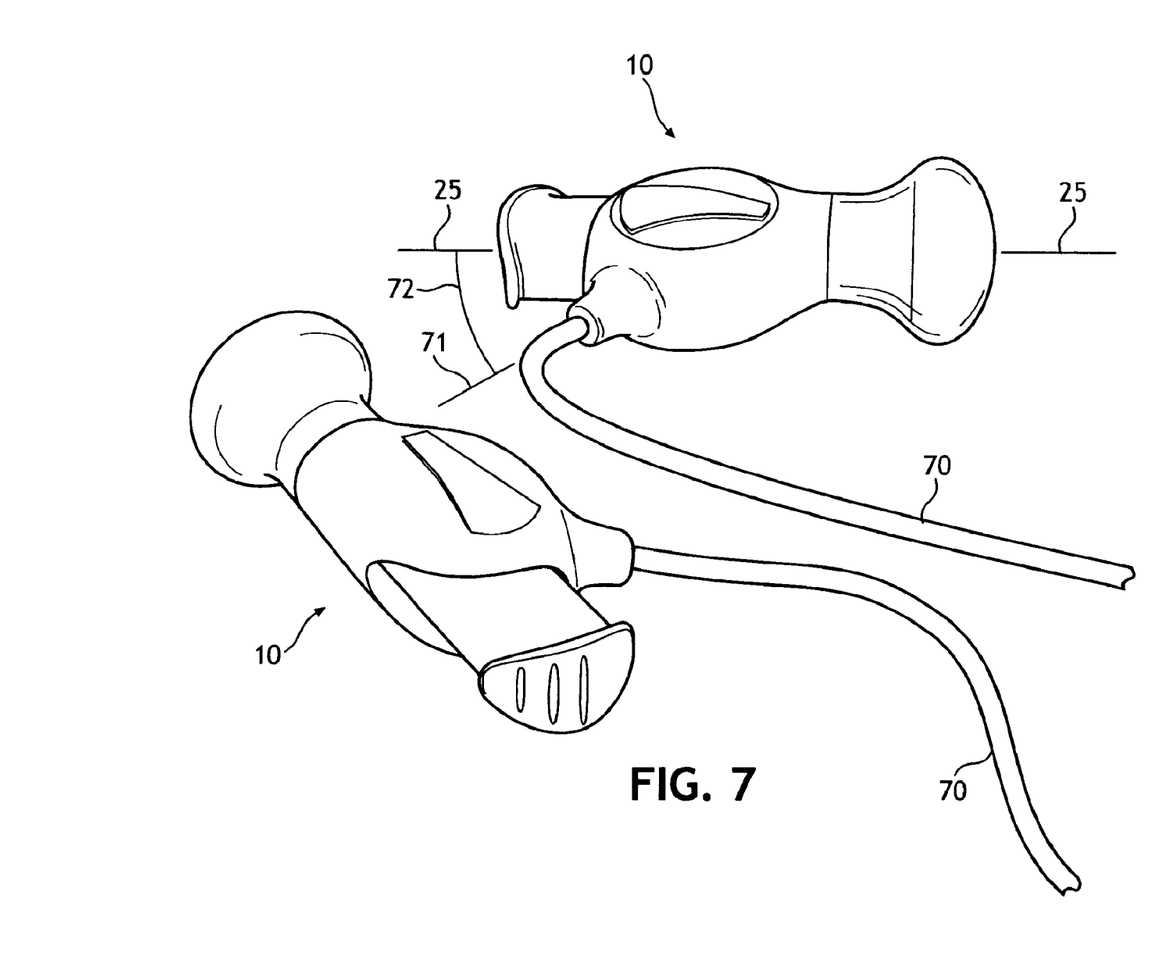
FIG. 7 is a perspective view of a pair of devices of the present invention in the at-rest position.
Figure 8:
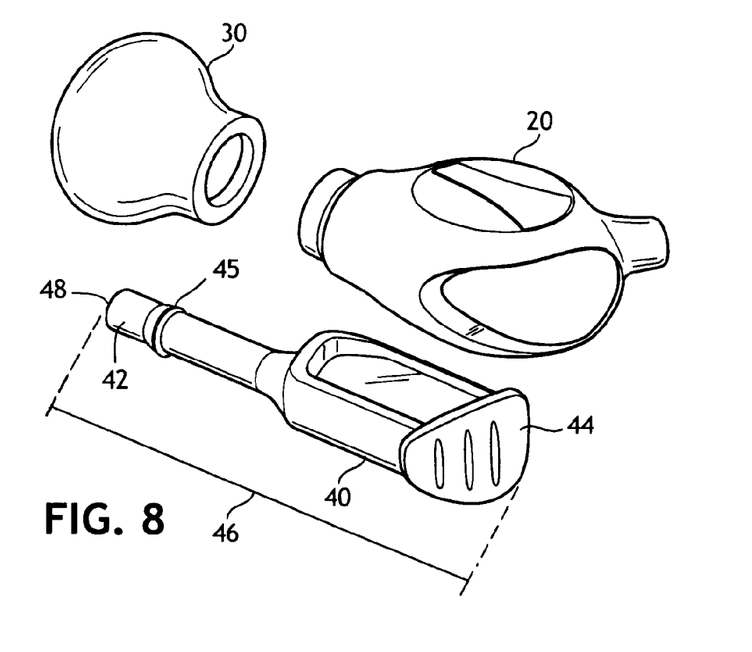
FIG. 8 is an exploded perspective view of one of the devices in FIG. 7.
Figure 9:
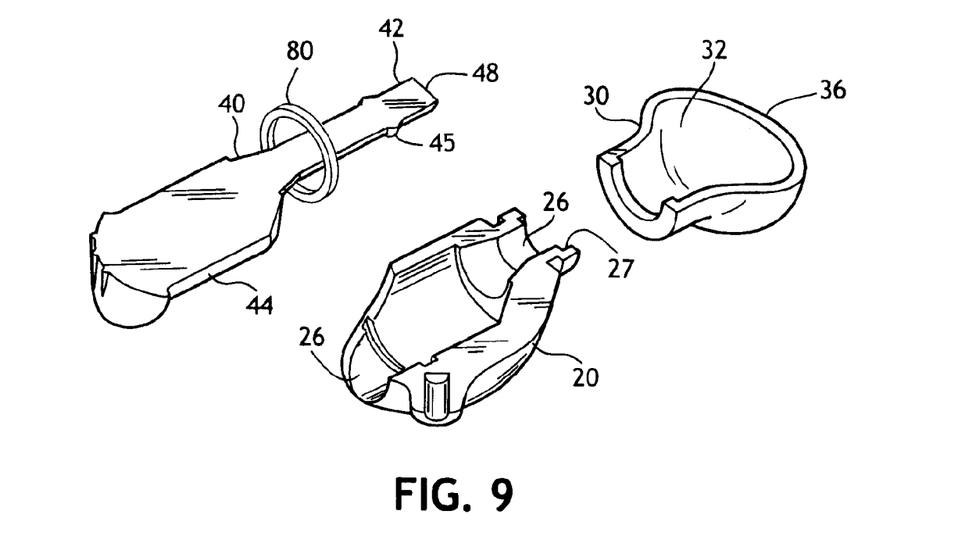
FIG. 9 is a cross-sectional side view of the parts of the device in FIG. 8.

Additional features relate to the body, plunger and bladder configurations, as well as others. In FIG. 7 is a pair of devices 10, and they are connected together by a lanyard 70 or other similar connection means for a variety of reasons, e.g., easy location when not in an ear canal, to help remove from the ear canal, to keep from falling into a user's work space, or the like. Device 10 may include lanyard 70 joined with body 20. Lanyard 70 may, advantageously though not required, be positioned such that an acute angle 72 between an axis 71 of lanyard 70 and the longitudinal axis 25 of shaft 26 is formed in the range of 80 degrees to 10 degrees. More advantageously in this regard, if desired, the acute angle may be in the range of 65 degrees to 35 degrees, and still more advantageously, if desired, acute angle 72 may be in the range of 50 degrees to 40 degrees.

As seen in FIGS. 8-10 and 12-14, plunger 40 may have an annular ring 45 to locate and/or maintain the plunger in the shaft 26 once located in shaft 26. Ring 45 may sit against seat 27 when the device is in the at-rest position, as seen in FIGS. 10 and 12-14. Ring 45 may be joined to a surface of the plunger and may seat against body 20, and advantageously the body ear end 22, at least when the plunger is in the in-ear position to create a seal between the chamber and at least a portion of the shaft 26. This can help prevent the transmission of sound through and/or along the shaft when the device is in use.

With reference to FIGS. 10 and 11, building further upon the seal and/or comfort advantages, the plunger 40 may be constantly tensioned toward the at-rest position. For example, constantly tensioned could be by an interference relationship between the plunger 40 and the body 20. Still further, this could be by way of an elastic band 80 joined to the plunger and a cooperating detent 28 located in the body adjacent the elastic band. Detent 28 slides in slot 29 to selectively engage band 80 when the plunger is pressed into the body.

Bladder 30 may have a combination or curved end 36 (FIGS. 12 and 14) or a substantially flat end 36 (FIG. 13). Also, bladder 30 may have curved sides 38 (FIGS. 12 and 14) or substantially flat sides 38 (FIG. 13). Bladder 30 may also have an additional flange 39 for enhanced sound reduction.

Plunger 40 may be configured such that at least 50% of its length 46, including the plunger ear end 42, travels only through movement that is parallel to shaft 26. This configuration and more parallel movement can provide an efficient and effective force for more easily actuating plunger 40, and in turn, bladder 30. Building on this advantage, in particular suitable aspects of increasing advantage, though not required, the at least 50% of length 46 may be at least 60%, at least 70%, at least 80%, at least 90%, or all of the length of the elongate plunger including the plunger ear end. Still further, additionally or alternatively, the elongate plunger may be actuated by a force 60 applied in a direction that is substantially parallel to the shaft, as in FIGS. 1-9. For example, the force may be applied to the plunger user end 44 of the elongate plunger.

It may be advantageous for enhanced sound reduction to have a fluid (e.g., gas, liquid, gel or similarly functioning material(s)) in chamber 32 of resilient bladder 30. As such, the fluid would be sealed from an environment 16 outside bladder 30. Alternatively, and generally, chamber 32 need not be sealed from the environment 16. The Figures showing device 10 in an assembled configuration enable chamber 32 to be sealed or unsealed, all dependent upon the nature of the seal between the bladder 30 and body ear end 22 and a sealed (yet movable) relationship between shaft 26 and plunger 40 which actuates inside the shaft to operate the bladder.

While not required, the invention may be advantageous for sound enhancement too, e.g., not only taking advantage of sound reduction capabilities but also hearing aid like capabilities. In this way, device 10 can be configured (not shown) to locate a microphone or the like in device 10 and help bring desired sound into the ear canal and/or locate a microphone in the ear canal better, e.g., via shaft 26 in communication with bladder 30.

In other aspects of the invention there is provided an ear canal self-fitting device method. The method includes providing the body 20 having body ear end 22 and opposite body user end 24 and shaft 26 extending from the ear end to the user end. The method also includes locating elongate plunger 40 in the shaft with the elongate plunger having plunger user end 44 extending out of the shaft and away from the body ear end and the plunger having opposite plunger ear end 42. The method further includes joining resilient bladder 30 with the body ear end of the elongate body and over the plunger ear end. In this way, the plunger ear end can be in communication with the resilient bladder, and the resilient bladder is deformable from the at-rest position to the in-ear position such that the resilient bladder has first cross-sectional area 50 in the at-rest position and second cross-sectional area 52 in the in-ear position, and optionally third cross-sectional area in the insertion position, with first cross-sectional area 50 being greater than second cross-sectional area 52, and if employed, second cross-sectional area 52 being greater than the third cross-sectional area.

The method still further includes actuating elongate plunger 40 between the at-rest position and the insertion position thereby assisting resilient bladder 30 to be deformed into the in-ear position when located in ear canal 12. The method can further include limiting at least 50% of the length 46 of the elongate plunger including the plunger ear end, to traveling only through movement that is parallel to shaft 26 when actuating the elongate plunger. Alternatively to, or in addition to, the previous step, the step of actuating the elongate plunger may be applying force 60 in the direction that is substantially parallel to shaft 26 (e.g., FIGS. 1-7). While not being required, it can be advantageous that the following steps occur in the following sequential order: providing, followed by locating, followed by joining, followed by actuating.

In practice, device 10 may be used as follows. Force 60 can be applied to plunger 40 (e.g., by a user's thumb and/or finger(s) or the like) at plunger user end 44, causing the plunger, i.e., incrementally, to go into shaft 26 at the plunger user end and thereby cause plunger ear end 42 to leave shaft 26 and engage resilient bladder 30, i.e., incrementally, from the at-rest position, then to the insertion position and then the in-ear position (in which the plunger has the same position as its at-rest position) when the force 60 is removed from the plunger. At this point, the device 10 would be located in ear canal 12 in a partially expanded condition to block the ear canal for sound optimization such as noise reduction and/or acoustic enhancement. In particular, the in-ear position of the bladder is determined by the user's particular ear canal shape and size and is therefore self-fitting or customizable.

Without being limited to a particular theory of understanding or noted advantageous features, the following features are discussed. The reduction in the cross-sectional area is converted into additional length of bladder 30 thus reducing the diametrical force exerted on small ear canals, thereby enhancing comfort even for smaller ear canals. Also, this diametrical reduction is achieved more conveniently than foam ear plugs and more effectively than for most ear plug types thus increasing the likelihood of proper insertion and more optimal protection, for all size ear canals. For removal, the device can be simply pulled out of the ear slowly and/or rotated in doing so, and it is removed. Also, with the features of the present invention it is made of sufficiently substantial materials and design so as to allow for multiple uses.

For a discussion of additional optional features for use with the invention, reference is made to assignee's prior filed application, of the same title, and having U.S. Ser. No. 11/799,344 filed Apr. 30, 2007 (aka PCT/IB2008/050922 filed Mar. 13, 2008), and assignee's co-filed application Ser. No. 12/217,041, also with the same title as this application, both of which are incorporated herein by reference.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A self-fitting device for location in an ear canal, comprising:
   a body having a body ear end, an opposite body user end, and a shaft extending from the ear end to the user end;
   a resilient bladder joined with the body ear end and a chamber defined inside the resilient bladder where the chamber is in communication with the shaft;
   an elongate plunger located in the shaft, the elongate plunger having a plunger user end extending out of the shaft and away from the body ear end and an opposite plunger ear end in communication with the chamber;
   the resilient bladder is deformable between an at-rest position and an in-ear position, such that the resilient bladder has a first cross-sectional area in the at-rest position and a second cross-sectional area in the in-ear position, wherein the first cross-sectional area is greater than the second cross-sectional area; and,
   the elongate plunger actuates between the at-rest position and an insertion position to assist the resilient bladder to be deformed into the in-ear position and wherein the plunger actuates in the insertion position without extending a front end portion of the bladder forward of a position of the front end portion when the bladder is in the at-rest position.

2. The device of claim 1 wherein the entire plunger ear end is spaced from the bladder at all times except when the plunger is in the insertion position.

3. The device of claim 1 wherein the plunger is constantly tensioned toward the at-rest position.

4. The device of claim 3 wherein constantly tensioned comprises an interference relationship between the plunger and the body.

5. The device of claim 4 wherein the interference relationship comprises an elastic band joined to the plunger and a cooperating detent located in the body adjacent the elastic band.

6. The device of claim 1 wherein an annular ring is joined to a surface of the plunger and seats against the body at least when the plunger is in the in-ear position to create a seal between the chamber and at least a portion of the shaft.

7. The device of claim 1 wherein actuation of the plunger occurs by application of a force in a direction that is substantially parallel to the shaft.

8. The device of claim 1 wherein at least 50% of a length of the elongate plunger, including the plunger ear end, travels only through movement that is parallel to a longitudinal axis of the shaft.

9. The device of claim 1 further comprising a lanyard joined with the body and wherein the lanyard is positioned such that an acute angle between the lanyard and the longitudinal axis of the shaft is formed in the range of 80 degrees to 10 degrees.

10. A self-fitting device for location in an ear canal, comprising:
    a body having a body ear end, an opposite body user end, and a shaft extending from the ear end to the user end;
    a resilient bladder joined with the body ear end and a chamber defined inside the resilient bladder where the chamber is in communication with the shaft;
    an elongate plunger located in the shaft, the elongate plunger having a plunger user end extending out of the shaft and away from the body ear end and an opposite plunger ear end in communication with the chamber;

the resilient bladder is deformable between an at-rest position and an in-ear position, such that the resilient bladder has a first cross-sectional area in the at-rest position and a second cross-sectional area in the in-ear position, wherein the first cross-sectional area is greater than the second cross-sectional area; and, the elongate plunger actuates between the at-rest position and an insertion position to assist the resilient bladder to be deformed into the in-ear position wherein the plunger actuates to engage the resilient bladder in the insertion position and actuates to separate from the resilient bladder in the in-ear position.

11. The device of claim 10 wherein the entire plunger ear end is spaced from the bladder at all times except when the plunger is in the insertion position.

12. The device of claim 10 wherein the plunger is constantly tensioned toward the at-rest position by an interference relationship between the plunger and the body.

13. The device of claim 10 wherein an annular ring is joined to a surface of the plunger and seats against the body at least when the plunger is in the in-ear position to create a seal between the chamber and at least a portion of the shaft.

14. The device of claim 10 wherein at least 50% of a length of the elongate plunger, including the plunger ear end, travels only through movement that is parallel to a longitudinal axis of the shaft.

15. The device of claim 10 wherein the resilient bladder is a foam material.

16. The device of claim 10 wherein the body is formed of a material having a first hardness value and the elongate plunger is formed of a material having a second hardness value, and the first hardness value is different than the second hardness value.

17. The device of claim 16 wherein the first hardness value is greater than the second hardness value.

18. A self-fitting device for location in an ear canal, comprising:
 a body having a body ear end, an opposite body user end, and a shaft extending from the ear end to the user end;
 a resilient bladder joined with the body ear end and a chamber defined inside the resilient bladder where the chamber is in communication with the shaft;
 an elongate plunger located in the shaft, the elongate plunger having a plunger user end extending out of the shaft and away from the body ear end and an opposite plunger ear end in communication with the chamber;
 the resilient bladder is deformable between an at-rest position and an in-ear position, such that the resilient bladder has a first cross-sectional area in the at-rest position and a second cross-sectional area in the in-ear position, wherein the first cross-sectional area is greater than the second cross-sectional area; and,
 the elongate plunger actuates between the at-rest position and an insertion position to assist the resilient bladder to be deformed into the in-ear position such that when the plunger is in the insertion position a tip of the plunger ear end engages the bladder and when the plunger is in the in-ear position the tip of the plunger ear end is spaced from the bladder.

19. The device of claim 18 wherein the entire plunger ear end is spaced from the bladder at all times except when the plunger is in the insertion position.

20. The device of claim 18 wherein the plunger is constantly tensioned toward the at-rest position by an interference relationship between the plunger and the body.

21. The device of claim 18 wherein an annular ring is joined to a surface of the plunger and seats against the body at least when the plunger is in the in-ear position to create a seal between the chamber and at least a portion of the shaft.

22. The device of claim 18 wherein at least 50% of a length of the elongate plunger, including the plunger ear end, travels only through movement that is parallel to a longitudinal axis of the shaft.

* * * * *